United States Patent [19]
Kanel et al.

[11] Patent Number: 5,900,504
[45] Date of Patent: * May 4, 1999

[54] NICKEL-CATALYZED CARBONYLATION PROCESS

[75] Inventors: Jeffrey Scott Kanel; Stanley John Okrasinski, both of Kingsport, Tenn.

[73] Assignee: Eastman Chemical Company, Kingsport, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/603,940

[22] Filed: Feb. 20, 1996

[51] Int. Cl.$^6$ ............................ C07C 51/10; C07C 67/36
[52] U.S. Cl. ........................ 562/519; 562/517; 560/232
[58] Field of Search ............................ 560/232; 562/517, 562/579

[56] References Cited

U.S. PATENT DOCUMENTS

| | | |
|---|---|---|
| 3,845,121 | 10/1974 | Eubanks et al. ..................... 260/532 |
| 4,252,741 | 2/1981 | Porcelli et al. . |
| 4,482,497 | 11/1984 | Rizkalla . |
| 4,659,518 | 4/1987 | Rizkalla et al. ..................... 260/413 |
| 5,237,097 | 8/1993 | Smith et al. . |

*Primary Examiner*—Jose'G. Dees
*Assistant Examiner*—Barbara Badio
*Attorney, Agent, or Firm*—Michael J. Blake; Charles R. Martin; Harry J. Gwinnell

[57] ABSTRACT

Disclosed is an improved liquid phase process for the preparation of an acetyl product comprising acetic acid, by the carbonylation of a carbonylatable reactant material comprising methanol, methyl acetate, dimethyl ether or a mixture thereof in the presence of a catalyst system comprising a nickel component and an iodide component. In the separation of the crude acetyl product mixture from a liquid containing the non-volatile catalyst components, precipitation of metals and other catalyst components is avoided or minimized by maintaining a hydrogen pressure of at least 0.34 bar absolute within the flash evaporator zone wherein the separation occurs.

5 Claims, No Drawings

NICKEL-CATALYZED CARBONYLATION PROCESS

This invention pertains to carbonylation processes using nickel catalysts. More specifically, this invention pertains to liquid phase processes wherein methanol, methyl acetate and/or dimethyl ether is carbonylated in the presence of a catalyst system comprising a nickel compound to produce acetic acid, methyl acetate and/or acetic anhydride.

Acetic acid traditionally has been manufactured by methods which rely upon the oxidation of either light hydrocarbons or ethylene-derived acetaldehyde. More recently, however, the homogeneously catalyzed carbonylation of methanol has proven to be the process of choice for the commercial production of acetic acid, and virtually all new manufacturing capacity makes use of this technology. This process typically employs a rhodium compound and various promoters to convert a mixture of methanol (or one of its derivatives) and carbon monoxide to acetic acid. See, for example, U.S. Pat. No. 3,769,329. The use of such an expensive Group VIII noble metal catalyst system imposes two requirements upon any commercial facility which utilizes it: (1) as much acetic acid as possible must be produced per unit of time for each rhodium-containing moiety present in the reactor (high turn-over and high rate), and (2) a means must be provided to efficiently recycle and recover any rhodium which escapes the confines of the reactor. Adherence to these constraints helps to assure that the lowest catalyst cost possible per unit of acetic acid produced will be attained.

To achieve this goal, much effort has been expended to identify the promoters and reaction conditions which optimize the behavior of the rhodium-based catalyst systems. In addition, techniques for the recovery and recycle of catalyst residues have been developed and implemented. Nevertheless, in spite of the great efficiency with which it is now possible to operate carbonylation units utilizing noble metal, e.g. rhodium, catalysts, the development of technology which avoids their use has been of on-going interest. The benefits of not using an expensive noble metal catalyst include (1) a substantial reduction in initial capital investment for the construction of a commercial manufacturing facility can be realized by avoiding the purchase of large quantities of a precious metal; (2) a further reduction in initial capital outlay occurs if the need for catalyst recovery and recycle equipment can be scaled back or eliminated; and (3) the recurring costs associated with the operation of these recovery and recycle units can be minimized or avoided entirely. These benefits represent a significant simplification and improvement in process technology, and they continue to drive the development of non-noble metal catalyst systems for the production of acetic acid.

In a commercial carbonylation process for the manufacture of acetic acid, methanol, water, carbon monoxide, a catalyst recycle stream comprising acetic acid and dissolved catalyst components, and, optionally, hydrogen are fed continuously to a reactor which is maintained at an elevated temperature and pressure which results in a liquid phase reaction medium. A crude, liquid product stream comprising acetic acid and dissolved catalyst components is removed continuously from the reactor and fed to a flash evaporator wherein, as the result of reducing the pressure, up to about 70 weight percent of the liquid product stream is vaporized and the non-vaporized portion of the liquid product stream comprising acetic acid and the non-volatile catalyst components is recycled to the carbonylation reactor. Fresh catalyst components are added to the process as needed to maintain a predetermined concentration of the components and process contaminants such as corrosion metals are removed as necessary. The liquid product vaporized in the flash evaporator is fractionated into acetic acid product which is removed from the process and low boiling components such as methanol, methyl iodide and methyl acetate which are recycled to the carbonylation reactor.

In the above-described process, the reactor vessel is operated at elevated temperature and pressure chosen to optimize the behavior of the catalyst system. The headspace of the reactor usually will contain hydrogen, carbon monoxide and vapor of the carbonylation reaction components. In the flash evaporator, the ambient pressure due to hydrogen and carbon monoxide is considerably lower than that of the reactor. In fact, any hydrogen or carbon monoxide present in the evaporator appears there only because it is dissolved in the crude, liquid product stream removed from the reactor. The continuous removal of vapor from the evaporator and the concomitant necessity to maintain the evaporator at a relatively low pressure results in carbon monoxide and hydrogen pressures that are much lower than pressures in the reactor. The relatively low hydrogen and carbon monoxide partial pressures existing in the evaporator and recycle lines coupled with the increase in concentration of the catalyst solution which occurs in the evaporator has the potential to result in precipitation of the nickel component of catalyst systems utilizing a nickel catalyst system. The precipitated nickel may bind to (plate onto) the walls of the evaporator and/or the recycle piping and thus be lost from the process. Recovery of the nickel thus lost from the production system is not economically practical. Furthermore, such process streams typically contain other metal compounds which arise from corrosion of the process vessels, tubing and valves. These corrosion metals themselves precipitate under these conditions or even promote the precipitation of catalyst components. Common corrosion metals may include iron, chromium, nickel, zirconium and/or molybdenum.

We have now discovered that by controlling the partial pressure of hydrogen in the evaporator the precipitation of nickel from nickel catalyst systems can be avoided or, at least, substantially minimized. This simple and unexpected means of maintaining nickel catalysts in a dissolved state can be applied under conditions in which product is being distilled from the reaction mixture. Under these conditions the avoidance of catalyst precipitation greatly facilitates both product removal and return of the catalyst residues to the reaction zone. The method has been shown to be effective even in the presence of very high levels of typical corrosion metals.

The present invention therefore comprises a continuous process for the preparation of an acetyl product comprising acetic acid which comprises the steps of:

(1) feeding (i) a carbonylatable reactant material comprising methanol, methyl acetate, dimethyl ether or a mixture thereof, (ii) a gas comprising carbon monoxide or a mixture of carbon monoxide and hydrogen, (iii) a catalyst recycle stream comprising acetic acid and dissolved catalyst components comprising a nickel component and an iodide component and (iv) optionally water, continuously to a carbonylation zone which is maintained at an elevated temperature and pressure which results in a liquid phase reaction medium, wherein acetyl product is formed and carbonylatable reactant is consumed;

(2) removing crude, liquid acetyl product stream comprising acetic acid and the dissolved catalyst components continuously from the reactor;

(3) feeding the crude, liquid acetyl product stream and hydrogen to a flash evaporator maintained at a pressure which is sufficiently less than the pressure within the reactor to effect vaporization of at least 10 to 70 weight percent of the liquid product stream to obtain a vapor stream comprising acetyl product and a liquid stream comprising acetic acid and the non-volatile catalyst components which is recycled to the carbonylation reactor;

wherein a hydrogen partial pressure of at least 0.34 bar absolute (5 pounds per square inch absolute, psia), preferably about 0.7 to 3.4 bar absolute (approximately 10 to 50 psia) is maintained in the flash evaporator. Pressure values are given herein in bars absolute unless specified otherwise. The use of hydrogen in conjunction with nickel-containing catalysts for the production of acetic acid from methanol (or one of its derivatives) has been described only within the confines of the primary carbonylation zone. In this context (i.e., the elevated temperature and pressure of the reaction zone) the presence of hydrogen is known to improve the rate of the carbonylation reaction. For nickel-containing catalyst systems in general, there are no previous reports of the use of hydrogen outside of the primary reaction zone nor is there any teaching regarding hydrogen's beneficial effects upon catalyst solubility or its ability to suppress catalyst precipitation.

The principle of the present invention also may be utilized in static holding vessels in which a solution of a nickel-containing catalyst system is being stored for some period of time at temperatures and pressures substantially lower than those normally found in the reaction zone of a carbonylation process such as that described herein. For example, catalyst-containing process solution might require temporary storage at total pressures of from about 1 bar (15 psia) to about 34.5 bar (500 psia) or, more preferably, at total pressures of about 3.4 bar (50 psia) to about 13.8 bar (200 psia). Such temporary storage may be necessitated by plant maintenance procedures or periodic pressure vessel inspections. Again, the reuse and physical manipulation of these solutions is greatly aided by the ability to maintain the nickel-containing catalyst system in solution.

A second embodiment of the present invention, therefore, is a process for stabilizing a carbonylation process liquid during the temporary storage thereof which comprises the steps of:

(1) removing from a carbonylation process a carbonylation process liquid comprising (i) acetic acid, (ii) methanol, methyl acetate, dimethyl ether, water or a mixture of two or more thereof and (iii) dissolved catalyst components comprising a nickel component and an iodide component; and (2) retaining the carbonylation process liquid in a vessel maintained at a total pressure of about 1 bar (15 psia) to 34.5 bar (500 psia) and a hydrogen partial pressure of at least 0.34 bar. As is indicated by the foregoing description, the carbonylation process liquid is obtained from a carbonylation process for the preparation of an acetyl product comprising acetic acid wherein a carbonylatable reactant material comprising methanol, methyl acetate, dimethyl ether or a mixture thereof is contacted at elevated temperature and pressure with a gas comprising carbon monoxide or a mixture of carbon monoxide and hydrogen wherein acetyl product is formed and carbonylatable reactant is consumed. The principle of the invention also may be useful in other situations and the application of the invention is not to be considered limited by the scope of these examples.

Descriptions of nickel-containing catalyst systems for carbonylation reactions fall into three categories:

(1) those in which hydrogen is not recognized to have any effect upon the reaction, and it is therefore excluded as a component of the reaction mixture;

(2) catalytic processes in which hydrogen is not recognized or taught to have any beneficial effect upon the reaction, but it is noted that no harmful effects would be expected to accrue by its presence; and (3) those systems in which hydrogen is taught to have a beneficial effect upon the rate of carbonylation and thus is considered to be a crucial component of the reaction. For example, carbonylation processes utilizing nickel catalysts which also contain either molybdenum or tungsten as well as an organo-phosphorus or organo-nitrogen compound and an iodide in the preparation of carboxylic acids, e.g., acetic acid, from an alcohol, e.g., methanol, are disclosed in U.S. Pat. No. 4,659,518. The catalysts disclosed in U.S. Pat. No. 4,659,518 were found to operate at moderate temperatures and pressures at commercially-acceptable rates without the addition of hydrogen to the reactor.

An improvement in the processes and catalyst systems described in U.S. Pat. No. 4,659,518 is disclosed in U.S. Pat. No. 4,661,631 and Published British Patent Application 2,121,794A wherein reaction rate is increased by the inclusion of hydrogen within the reaction zone. This beneficial effect resulting from the presence of hydrogen in the reaction zone also has been noted in the carbonylation of alcohols in the presence of a catalyst system comprising nickel, an iodide and a tin compound (U.S. Pat. No. 4,134,912) as well as when the tin compound is replaced with a trivalent phosphorus compound (U.S. Pat. No. 4,356,320).

Carbonylation processes utilizing other catalyst systems comprising nickel, an iodide and a third component include those containing either vanadium (U.S. Pat. No. 4,436,889), chromium (U.S. Pat. No. 4,351,953), alkali metals (European Patent Specification EP 35,458) or lanthanide compounds (U.S. Pat. No. 4,426,537) as additional promoters. These disclosures do not note any beneficial effects resulting from the presence of hydrogen in the reaction zone, but they teach that no harmful effects arise as a result of its presence. In addition, several disclosures indicate that the presence of hydrogen in the reaction zone causes no untoward effect and further note that it may act to stabilize the catalyst (U.S. Pat. No. 4,482,497 and British Patent 2,128, 609). All of these patent publications teach that the effect of hydrogen in non-noble metal catalyzed carbonylations is limited to carbonylation rate enhancement in the reaction zone. In particular, there is no teaching regarding any beneficial effect upon nickel solubility or of the importance of maintaining hydrogen in contact with nickel-containing solutions outside of the reaction zone.

Although the behavior of rhodium-containing carbonylation catalysts is substantially different from that of nickel-containing catalysts, hydrogen also is known to enhance the rate of reaction in such systems. In stark contrast with the nickel-containing catalyst systems,—for the production of acetic acid—however, is the disclosure of U.S. Pat. No. 4,252,741 that carbon monoxide can be used to maintain catalyst solubility (hydrogen additionally may be present as an aid in maintaining reaction rate) and its use outside of the reaction zone has been described for a system in which methyl acetate is converted to acetic anhydride. Furthermore, in order to maintain rhodium-based catalyst systems for the manufacture of acetic acid in a dissolved state, the importance of maintaining appropriate levels of methyl acetate and iodide ion (U.S. Pat. No. 4,994,608) as well as organo-nitrogen (U.S. Pat. No. 4,433,165) or tin compounds (U.S. Pat. No. 4,433,166), within the reaction zone, has been described. An additional example of the use of carbon monoxide to avoid precipitation of rhodium-containing catalysts is seen in U.S. Pat. No. 5,237,097. This contrasting behavior of rhodium-based catalyst systems further illustrates the unexpected and novel nature of the present invention.

Thus, in accordance with the invention, carbon monoxide, optionally in the presence of hydrogen, is reacted with a mixture of (1) a carbonylatable material comprising methanol, methyl acetate, dimethyl ether or a mixture thereof and (2) an iodide compound to produce an acetyl product comprising acetic acid. When acetic acid is the desired product, the carbonylation is carried out in the presence of water. Acetic acid can be prepared effectively in a representative case by subjecting methanol to carbonylation. Alternatively, acetic acid may be obtained by carbonylating other carbonylatable compounds such as methyl acetate and/or dimethyl ether in the presence of equivalent amounts of water. The reaction is suitably carried out in a reaction zone to which the carbon monoxide, the alcohol, the iodide, the catalyst, any co-catalyst and, optionally, hydrogen are fed.

It is possible to operate the carbonylation process over a wide range of temperatures and pressures. For example, temperatures of about 150 to 250° C. may be used with temperatures in the range of about 180 to 250° C. being preferred. Temperatures in the range of about 200 to 225° C. are most preferred. Temperatures lower than those mentioned can be used but they tend to lead to reduced reaction rates, and higher temperatures may also be employed but there is no particular advantage in their use.

The process usually will be carried out at total pressures in the range of about 27 to 173 bar (approximately 400 to 2500 psia), preferably about 34.5 to 120 bar (approximately 500 to 1750 psia). The time of reaction is not a parameter of the process and depends largely upon the temperature employed, but typical residence times, by way of example, will generally fall in the range of 0.1 to 20 hours.

Although not necessary, the process typically is carried out in the presence of a solvent or diluent such as acetic acid. Alternatively, the solvent or diluent may be any organic solvent which is inert in the environment of the process such as hydrocarbons, e.g., octane, benzene, toluene, xylene, tetralin and the like. Mixtures of solvents can also be used, such as mixtures of methyl acetate and acetic acid. The carboxylic acid, when used, should preferably correspond to the acid being produced since, as indicated above, the preferred solvent is one that is indigenous to the system, e.g., acetic acid and/or methyl acetate in the case of methanol carbonylation. A solvent or diluent, when not the product itself, is suitably selected which has a boiling point sufficiently different from the desired product in the reaction mixture so that it can be readily separated, as will be apparent to persons skilled in the art.

The carbon monoxide preferably is employed in substantially pure form, as available commercially, but inert diluents such as carbon dioxide, nitrogen, methane, and noble gases can be present if desired. Hydrogen also may be contained in the carbon monoxide. The presence of inert diluents does not affect the carbonylation reaction but their presence makes it necessary to increase the total pressure in order to maintain the desired CO partial pressure. Indeed, in order to obtain low CO partial pressures the CO fed may be diluted with hydrogen or any inert gas such as those mentioned above. The presence of hydrogen does not lead to the formation of reduction products. When hydrogen is used, it typically will comprise up to about 25 volume percent, preferably about 2 to 10 volume percent, of the gas fed to the carbonylation zone. The presence of minor amounts of water such as may be found in the commercial forms of the reactants is entirely acceptable. Hydrogen, which may be present depending upon the nature of the catalyst employed, may be supplied as a pure component or as a mixture with carbon monoxide. Its presence in the reactor may enhance the rate of the carbonylation reaction or tend to stabilize the catalyst. The hydrogen supplied to the flash evaporator or static holding tank may be a pure component, a mixture of hydrogen and carbon monoxide, or a mixture of hydrogen and inert components such as nitrogen, carbon dioxide or helium. The hydrogen supply may be a hydrogen-rich stream already available in the process.

Examples of the nickel-containing catalyst systems which may be employed in the present invention include those described in the following U.S. patents:

U.S. Pat. No. 4,002,677—nickel; chromium; and tin;

U.S. Pat. No. 4,002,678—nickel; chromium; and a trivalent nitrogen or phosphine compound;

U.S. Pat. No. 4,134,912—nickel and tin;

U.S. Pat. No. 4,335,059 and U.S. Pat No. 4,659,518—nickel; molybdenum or tungsten; and a trivalent nitrogen or phosphine compound;

U.S. Pat No. 4,356,320—nickel and a trivalent nitrogen or phosphine compound; and U.S. Pat. No. 4,482,497 and U.S. Pat. No. 4,483,804—nickel; molybdenum or tungsten; and an alkali metal.

The particular catalyst system utilized is not a critical feature since the principle involved in the present invention is believed to be useful in carbonylation processes employing various nickel catalyst systems.

The co-catalyst components can be employed in any convenient form. For example, the nickel and the molybdenum or tungsten can be the metals themselves in finely-divided form, or a compound, both organic or inorganic, which is effective to introduce these co-catalyst components into the reaction system. Thus, typical compounds include the carbonate, oxide, hydroxide, bromide, iodide, chloride, oxyhalide, hydride, lower alkoxide (methoxide), phenoxide, or Mo, W or Ni carboxylates wherein the carboxylate ion is derived from an alkanoic acid of 1 to 20 carbon atoms such as acetates, butyrates, decanoates, laurates, benzoates, and the like. Similarly, complexes of these co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Particularly preferred are the elemental forms, compounds which are halides, especially iodides, and organic salts, e.g., salts of the monocarboxylic acid corresponding to the acid being produced.

The alkali metal component, e.g., a metal of Group IA of the Periodic Table such as lithium, potassium, sodium, and cesium, is suitably employed as a compound, especially a salt, and most preferably a halide, e.g., an iodide. The preferred alkali metal is lithium. The alkali metal component can, however, also be employed as the hydroxide, carboxylate, alkoxide or in the form of other convenient compounds such as are referred to above in connection with the other co-catalyst components, and typical alkali metal components are illustrated by sodium iodide, potassium iodide, cesium iodide, lithium iodide, lithium bromide, lithium chloride, lithium acetate, and lithium hydroxide.

The organo-phosphorus promoter preferably is a phosphine, e.g. of the formula

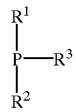

wherein $R^1$, $R^2$ and $R^3$ may be the same or different, and are alkyl, cycloalkyl, aryl groups, amide groups, e.g., hexamethyl phosphorus triamide, or halogen atoms, preferably containing 1 to 20 carbon atoms in the case of alkyl and cycloalkyl groups and 6 to 18 carbon atoms in the case of aryl groups. Typical hydrocarbyl phosphines include trimethylphosphine, tripropylphosphine, tricyclohexylphosphine and triphenylphosphine. Preferably the organo-nitrogen promoter is a tertiary amine or a polyfunctional nitrogen-containing compound, such as an amide, a hydroxy amine, a keto amine, a di-, tri- or other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexylmethylamine, 2,6-diaminopyridine, 2-quinolinol, N,N-diethyltoluamide, imidazole, and N-methylimidazole.

Although generally the organic promoter is added separately to the catalyst system, it is also possible to add it as a complex with any of the co-catalyst metals, such as bis(triphenylphosphine) nickel dicarbonyl and tetrakis (triphenyl phosphite) nickel. Both free organic promoters and complexed promoters can be used. When a complex of the organic promoter and the co-catalyst metal is used, free organic promoter can also be added.

It will be understood that the above-mentioned compounds and complexes are merely illustrative of suitable forms of the several co-catalyst components and are not intended to be limiting. The specified co-catalyst components employed may contain impurities normally associated with the commercially available metal or metal compounds and need not be purified further.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 millimole to 1 mole per liter of reaction mixture, preferably 1 millimole to 500 millimoles per liter and most preferably 1 millimole to 150 millimoles per liter.

The ratio of nickel to the molybdenum, or tungsten co-catalyst component can vary. Typically, it is one mole of the nickel component per 0.01 to 100 moles of the second co-catalyst component, i.e., the molybdenum, or tungsten, component, preferably the nickel component is used in the amount of 1 mole per 0.1 to 20 moles, most preferably 1 mole per 1 to 10 moles of the second co-catalyst component. Similarly, the ratio of nickel to the alkali metal component can vary, e.g., one mole of nickel per 1 to 1000 moles of alkali metal component, preferably 10 to 100 and most preferably 20 to 50.

The amount of iodide component may also vary widely but, in general, it should be present in an amount of at least 0.1 mole (expressed as I) per mole of nickel. Typically, there are used 1 to 100 moles of the iodide per mole of nickel, preferably 2 to 50 moles per mole. Ordinarily, more than 200 moles of iodide per mole of nickel are not used. It will be understood, however, that the iodide component does not have to be added to the system as a hydrocarbyl iodide but may be supplied as another organic iodide or as the hydroiodide or other inorganic iodide, e.g., a salt, such as the alkali metal or other metal salt, or even as elemental iodine.

As is specified above, Step (3) of the process of this invention involves feeding the crude, liquid acetyl product stream and hydrogen to a flash evaporator maintained at a pressure which is sufficiently less than the pressure within the reactor to effect vaporization of at least 10 to 70 weight percent of the liquid product stream to obtain a vapor stream comprising acetyl product and a liquid stream comprising acetic acid and the non-volatile catalyst components which is recycled to the carbonylation reactor. The total pressure in the flash evaporator may be in the range of about 1 bar (15 psia) to 10.3 bar (150 psia) although it preferably is in the range of about 2 bar (30 psia) to 5.2 bar (75 psia). Heat can be added or removed or the flash distillation can be carried out adiabatically, as will be apparent to those skilled in the art. An adiabatic flash distillation employed in connection with the preparation of acetic acid is described in U.S. Pat. No. 3,845,121. In accordance with the invention, during the flash distillation or evaporation of the volatile components from the liquid containing the non-volatile catalyst components, a hydrogen partial pressure of at least 0.34 bar absolute is maintained within the flash evaporator vessel. The hydrogen partial pressure within the flash evaporator vessel preferably is maintained at about 0.7 to 3.4 bars absolute.

The vapor stream obtained from the flash evaporation zone is distilled to separate the more volatile components such as alkyl iodide and unreacted reactants (methanol and/or dimethyl ether) and co-products such as methyl acetate from the acetic acid. The crude product material can be further refined to separate the crude acetyl product mixture into its individual components.

The process provided by the present invention preferably is employed in the manufacture of acetic acid by the carbonylation of a mixture of methanol, water and an iodine component, typically methyl iodide. This preferred embodiment therefore comprises the steps of:

(1) feeding (i) methanol, (ii) a gas comprising carbon monoxide or a mixture of carbon monoxide and hydrogen, (iii) a catalyst recycle stream comprising acetic acid and dissolved catalyst components comprising a nickel component and an iodide component and (iv) water, continuously to a carbonylation zone which is maintained at an elevated temperature and pressure which results in a liquid phase reaction medium, wherein acetic acid product is formed and methanol is consumed;

(2) removing crude, liquid acetic acid product stream and the dissolved catalyst components continuously from the reactor;

(3) feeding the crude, liquid acetic acid product stream and hydrogen to a flash evaporator maintained at a pressure which is sufficiently less than the pressure within the reactor to effect vaporization of at least 10 to 70 weight percent of the liquid product stream to obtain a vapor stream comprising acetyl product and a liquid stream comprising acetic acid and the non-volatile catalyst components which is recycled to the carbonylation reactor;

wherein a hydrogen partial pressure of about 0.7 to 3.4 bar is maintained in the flash evaporator. The preferred catalyst system comprises nickel, molybdenum, and a phosphine such as triphenylphosphine or a lithium compound.

The process of the present invention is further illustrated by the following examples which are provided for a fuller understanding of the invention but it should be understood that they are given for illustrative purposes only and are not to be interpreted as limiting the invention in any way.

COMPARATIVE EXAMPLE 1

A 1.8-liter, stirred autoclave was used in batch mode as both the reactor and flash separation unit for the carbonylation of methanol to acetic acid. A mixture of 265 mL methanol, 55 mL methyl acetate, 85 mL methyl iodide, 175 mL acetic acid, 50 mL water, 6.3 g molybdenum hexacarbonyl, 2.37 g iron(II) acetate, 7.87 g chromium acetate, basic, 7.3 g nickel acetate-4-hydrate and 59.5 g triphenylphosphine were initially charged to the autoclave. The atmosphere was purged by pressurizing with CO (13.8 bar gauge, 200 psig) and venting, twice. The system was then charged with a mixture of CO (34.5 bar gauge, 500 psig) and hydrogen (6.9 bar gauge, 100 psig), heated to 200° C. and the final pressure adjusted to 89.6 bar gauge (1300 psig) with CO. The pressure was maintained at this value by the addition of Co. After 5 hours, the autoclave was cooled to 150° C., and the reaction mixture flashed from the autoclave until a pressure of 3.4 bar gauge (50 psig) was reached. The remaining liquid-phase reaction mixture was then transferred to a glass autoclave, preheated to 150° C. This transfer process resulted in a reduction of the pressure to approximately 2.3 bar gauge (33 psig). This glass autoclave was equipped with a drain line containing a 0.45 micron filter through which samples of the reaction mixture could be obtained. Removal and examination of the filter allowed the detection of solids in the reaction mixture. By varying the temperature of the glass autoclave the solubility limit of the reaction mixture, referred to as the precipitation temperature, could be determined.

In this example, the precipitation temperature was 65° C. Before filtration the reaction mixture contained 2850 ppm molybdenum, 7750 ppm total metals and the ratio (weight) of phosphorus to total metals in the solution was found to be 1.3:1. No hydrogen was added to the system after transfer to the glass autoclave.

EXAMPLE 1

The experimental apparatus and procedure described in Comparative Example 1 were utilized with the following changes. A mixture of 265 mL methanol, 55 mL methyl acetate, 85 mL methyl iodine, 175 mL acetic acid, 46.9 g water, 6.3 g molybdenum hexacarbonyl, 4.72 g iron(II) acetate, 15.7 g chromium acetate, basic, 7.3 g nickel acetate-4-hydrate and 59.2 g triphenylphosphine were charged initially to the autoclave. After flashing, the reaction mixture was charged to the glass autoclave and hydrogen was added (1.4 bar gauge, 20 psig). During the course of the experiment, temperature changes and the removal of sample aliquots would alter the pressure within the glass autoclave. A constant pressure was maintained by the further addition of hydrogen, as necessary.

The precipitation temperature was 25° C. Before filtration the reaction mixture contained 2025 ppm molybdenum, 16090 ppm total metals and the ratio (weight) of phosphorus to total metals was found to be 1.1:1. The solids were found to contain nickel, iron, chromium, phosphorus and iodine. Note the improved catalyst solubility in this example compared to that in Comparative Example 1 despite the elevated concentration of total metals (16090 ppm to 7750 ppm). Both the molybdenum concentration and the ratio of phosphorus to total metal concentration are similar for these two examples.

COMPARATIVE EXAMPLE 2

The experimental apparatus and procedure described in Comparative Example 1 was utilized with the following changes: A mixture of 265 mL methanol, 55 mL methyl acetate, 85 mL methyl iodide, 175 mL acetic acid, 36.6 g water, 6.3 g molybdenum hexacarbonyl, 7.12 g iron(II) acetate, 23.6 g chromium acetate, basic, 7.3 g nickel acetate-4-hydrate and 59.5 g triphenylphosphine were initially charged to the autoclave.

The precipitation temperature was 97° C., and the precipitated solids contained phosphorus, iodine, iron, and chromium. Before filtration the reaction mixture contained 3570 ppm molybdenum, 17080 ppm total metals and the ratio (weight) of phosphorus to total metals was found to be 0.58:1. In this experiment hydrogen was not added to the system after transfer to the glass autoclave.

EXAMPLE 2

The experimental apparatus and procedure described in Comparative Example 1 were utilized with the following changes: A mixture of 265 mL methanol, 55 mL methyl acetate, 85 mL methyl iodide, 175 mL acetic acid, 46.9 g water, 6.3 g molybdenum hexacarbonyl, 7.12 g iron(II) acetate, 23.6 g chromium acetate, basic, 7.3 g nickel acetate-4-hydrate and 59.2 g triphenylphosphine were initially charged to the autoclave. Hydrogen was charged to the glass autoclave following the procedure set forth in Example 2.

The precipitation temperature was 810C. Before filtration the reaction mixture contained 4370 ppm molybdenum, 22,470 ppm total metals and the ratio (weight) of phosphorus to total metals was found to be 0.53:1. The solids were found to contain iron, nickel, chromium, molybdenum, phosphorus and iodine. Improved catalyst solubility resulted despite the elevated concentration of both total metals (22,470 ppm compared to 17,080 ppm) and molybdenum (4370 ppm compared to 3570 ppm) at an approximately constant phosphorus to total metal ratio.

The invention has been described in detail with particular reference to preferred embodiments thereof, but it will be understood that variations and modifications can be effected within the spirit and scope of the invention.

We claim:

1. Process for stabilizing a carbonylation process liquid during the temporary storage thereof which comprises the steps of:

(1) removing from a carbonylation process a carbonylation process liquid comprising (i) acetic acid, (ii) methanol, methyl acetate, dimethyl ether, water or a mixture of two or more thereof and (iii) dissolved catalyst components comprising a nickel component and an iodide component; and (2) retaining the carbonylation process liquid in a vessel maintained at a total pressure of about 1 to 34.5 bar and a hydrogen partial pressure of at least 0.34 bar.

2. Process according to claim 1 wherein the vessel is maintained at a total pressure of about 3.4 to 13.8 bar.

3. A process according to claim 1 wherein the hydrogen partial pressure of the vessel is maintained at about 0.7 to 3.4 bar.

4. A process according to claim 2 wherein the hydrogen partial pressure of the vessel is maintained at about 0.7 to 3.4 bar.

5. A process according to claim 1 wherein the hydrogen partial pressure of the vessel is maintained at about 0.7 to 3.4 bar, and the catalyst components comprise a nickel component, an iodide component, a molybdenum component, and a phosphine.

* * * * *